(12) United States Patent
Singer et al.

(10) Patent No.: US 6,203,986 B1
(45) Date of Patent: Mar. 20, 2001

(54) VISUALIZATION OF RNA IN LIVING CELLS

(76) Inventors: Robert H. Singer, 144 E. 8th St., Apt. 9D, New York, NY (US) 10028; Edouard Bertrand, 190 Allée du nouveau monde, Batm "Le Rochambeau", 34000 Montpellier (FR)

( * ) Notice: Subject to any disclaimer, the term of this patent is extended or adjusted under 35 U.S.C. 154(b) by 0 days.

(21) Appl. No.: 09/177,268

(22) Filed: Oct. 22, 1998

(51) Int. Cl.[7] .............................. A61B 10/00; C12Q 1/68; C12N 15/40
(52) U.S. Cl. .............................. 435/6; 435/7.21; 435/7.6; 435/69.1; 435/69.7; 435/91.4; 435/455; 435/320.1; 436/172
(58) Field of Search .............................. 435/6, 7.31, 7.8, 435/69.1, 69.7, 455, 476, 254.11, 320.1, 968

(56) References Cited

U.S. PATENT DOCUMENTS 5,834,184 * 11/1998 Harada et al. .............................. 435/6
5,965,368 * 10/1999 Vidal et al. .............................. 435/6

OTHER PUBLICATIONS

Bertrand et al, Localization of ASH1 mRNA Particles in Living Yeast, Molecular Cell, vol. 2, Oct. 1998, Publicly available Oct. 24, 1998.*

Wang et. al., Implications for bcd mRNA localization, Nature 369, p. 400–403, Jun. 2, 1994.*

Venkatesan et. al., Human Immunodeficiency Virus Type 1 Rev . . . , Journal of Virology 66(12) p. 7469–7480, Dec. 1992.*

Arn et al., "Motors Driving mRNA Localization: New Insights from In Vivo Imaging", Cell 95:151–154, 1998.*

Chalfie, "Green Fluorescent Protein", Photochemistry and Photobiology 62:651–656, 1995.*

Cormack et al., "Yeast–enhanced Green Fluorescent Protein (yEGFP): A Reporter of Gene Expression in Candida Albicans", Microbiology 143:303–311, 1997.*

Cubitt et al., "Understanding, Improving and Using Green Fluorescent Proteins", Trends Biochem Sci. 20(11):448–55, 1995.*

Fouts et al., "Functional Recognition of Fragmented Operator Sites by R17/MS2 Coat Protein, A Translational Repressor", Nucleic Acids Research 25:4464–4473, 1997.*

Larrick et al., "Green Fluorescent Protein: Untapped Potential in Immunotechnology", Immunotechnology 1(2):83–86, 1995.*

Lesser et al., "Mutational Analysis of Pre–mRNA Splicing in *Saccharomyces Cerevisiae* Using a Sensitive New Reporter Gene, CUP1", Genetics 133:851–863, 1993.*

Long et al., "Spatial Consequences of Defective Processing of Specific Yeast mRNAs Revealed by Fluorescent In Situ Hybridization", RNA 1:1071–1078, 1995.*

Prasher, "Using GFP to See the Light", Trends Genet 11(8):320–323, 1995.*

Samarsky et al., "The snoRNA Box C/D Motif Directs Nucleolar Targeting and Also Couples snoRNA Synthesis and Localization", The EMBO Journal 17:3747–3757, 1998.*

Sengupta et al., "A Three–hybrid System to Detect RNA–protein Interactions In Vivo", Proc. Natl. Acad. Sci. 93:8496–8501, 1996.*

Singer et al., "Methods and Materials to Visualize RNA in Living Cells", Albert Einstein College of Medicine hhttp://www.aecom.yu.edu/oil.*

Straight et al., "Mitosis in Living Budding Yeast: Anaphase A But No Metaphase Plate", Science 277:574–578, 1997.*

Valegard et al., "The Three–dimensional Structures of Two Complexes Between Recombinant MS2 Capsids and RNA Operator Fragments Reveal Sequence–specific Protein–RNA Interactions", J. Mol. Biol. 270:724–738, 1997.*

* cited by examiner

*Primary Examiner*—David Guzo
*Assistant Examiner*—Jon Shuman
(74) *Attorney, Agent, or Firm*—Fish & Richardson, P.C.

(57) ABSTRACT

A method for visualizing the location and movement of a specific RNA of interest in a living cell, in real time, is disclosed. The method includes the following steps: (a) providing a DNA encoding the RNA, which RNA includes a protein-binding site; (b) providing a nucleic acid encoding a fusion protein, which fusion protein comprises a fluorescent domain and an RNA-binding domain; (c) introducing the DNA encoding the RNA, and the nucleic acid encoding the fusion protein, into a eukaryotic cell so that the DNA encoding the RNA and the nucleic acid encoding the fusion protein are expressed in the cell; and (d) detecting fluorescence outside the nucleus or inside the nucleus of the cell, with the fluorescence being from the fusion protein bound to the RNA. In some embodiments, the fusion protein also includes an intracellular localization domain.

22 Claims, 3 Drawing Sheets

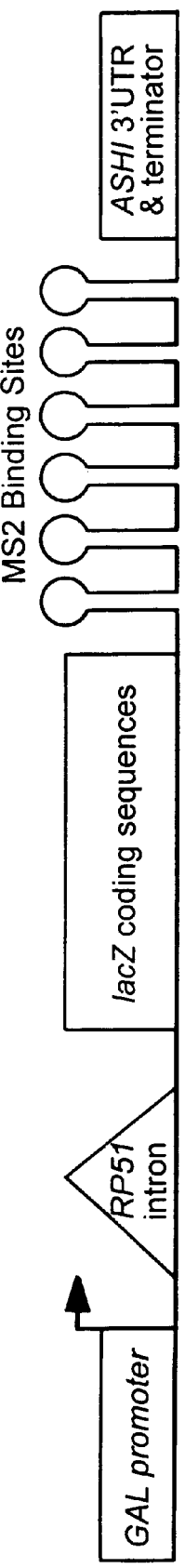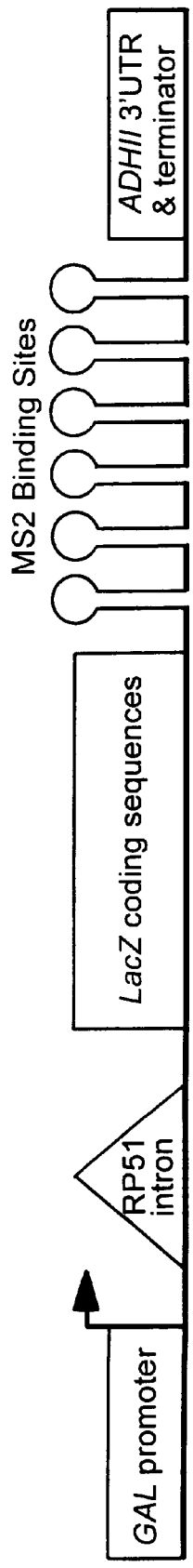
FIG. 1A
FIG. 1B

VISUALIZATION OF RNA IN LIVING CELLS

STATEMENT AS TO FEDERALLY SPONSORED RESEARCH

Work on this invention was supported by NIH Grant Nos. GM 54887 and GM 57071. Therefor the government has certain rights in the invention.

FIELD OF THE INVENTION

The invention relates to cell biology, genetics, recombinant DNA technology, fluorescence microscopy, and videography.

BACKGROUND OF THE INVENTION

Messenger RNA localization is a well-documented phenomenon and provides a mechanism by which to generate cell assymetry (St. Johnston, *Cell* 81:161–170 (1995); Glotzer et al., *Cell Dev. Biol.* 7:357–365 (1996); Steward et al., in *mRNA Metabolism and Posttranscriptional Gene Regulation*, Wiley-Liss, New York, 127–146). Messenger RNA localization has been studied by fluorescence in situ hybridization (FISH) (Long et al., *RNA* 1:1071–1078 (1995). In situ hybridization, and other methods that require fixation of cells, offer good spatial resolution, but are severely limited in temporal resolution. Thus, while these techniques are well-suited for determining where RNA goes in living cells, they are unsuited for determining how quickly, or by what route, the RNA travels to its destination.

A further limitation of FISH methods, is that fixation kills cells. Therefore, those methods are incompatible with cell selection, where cells must be kept alive to initiate a new cell line.

SUMMARY OF THE INVENTION

We have developed a general method for visualizing the location and movement of a specific RNA of interest in a living cell, in real time. The method includes the following steps: (a) providing a DNA encoding the RNA, which RNA includes a protein-binding site; (b) providing a nucleic acid encoding a fusion protein that includes a fluorescent domain and an RNA-binding domain that binds to the protein-binding site in the RNA; (c) introducing the DNA encoding the RNA, and the nucleic acid encoding the fusion protein, into a eukaryotic cell so that the DNA encoding the RNA and the nucleic acid encoding the fusion protein are expressed in the cell; and (d) detecting fluorescence in the cell, the fluorescence being from the fusion protein bound to the RNA.

Preferably, the RNA includes a multiplicity of protein-binding sites located in the 3' untranslated region (3'UTR) of the RNA. The RNA-binding domain can be derived from a bacteriophage MS2 protein, and the protein-binding site can be a bacteriophage MS2 binding site. In preferred embodiments of the invention, the fluorescent domain is derived from green fluorescent protein (GFP). In some embodiments, the fusion protein includes an intracellular localization domain, e.g., a nuclear localization signal (NLS) domain or a nuclear export signal (NES) domain. When the fusion protein contains an NLS domain, fluorescence from the fusion protein bound to the RNA is detected outside the nucleus.

The DNA encoding the RNA, and the nucleic acid encoding the fusion protein, can be provided on a single vector or on separate vectors. In some embodiments of the invention, the cell is a yeast cell. The cell can contain one or more RNA localization factors, e.g., she gene products in a yeast cell.

The invention also provides a method for screening a DNA library to detect a DNA encoding an RNA containing a protein-binding site. The method includes providing a eukaryotic test cell. The test cell expresses a fusion protein containing a fluorescent domain and an RNA-binding domain that binds to a protein-binding site. The method further includes transforming the test cell with a candidate DNA from the DNA library; and detecting the fusion protein bound to an RNA containing the protein-binding site, if present, by measuring fluorescence. In some embodiments, the fusion protein includes an intracellular localization domain, e.g., a nuclear localization signal (NLS) domain or a nuclear export signal (NES) domain. Preferably, the test cell does not express an endogenous protein that binds to the protein-binding site.

The invention also provides a nucleic acid encoding a fusion protein. The fusion protein encoded contains a fluorescent domain and an RNA-binding domain. The fluorescent domain can be derived from GFP or a GFP variant, e.g., blue fluorescent protein (BFP), yellow fluorescent protein (YFP), or cyan fluorescent protein (CFP). The binding domain can be derived from a bacteriophage MS2 binding protein. In some embodiments, the fusion protein includes an intracellular localization domain, e.g., a nuclear localization signal (NLS) domain or a nuclear export signal (NES) domain. The invention also includes a vector containing the nucleic acid encoding the fusion protein, and a cell transformed with the vector containing the nucleic acid encoding the fusion protein.

The invention also includes a screening method for identifying a compound that inhibits nuclear RNA export or import. The method includes providing a eukaryotic test cell that expresses a DNA encoding an RNA, which RNA includes a protein-binding site; and expresses a fusion protein. The fusion protein includes a fluorescent domain and an RNA-binding domain that binds to the protein-binding site in the RNA. The method further includes contacting the test cell with a candidate compound, and then detecting a candidate compound-related reduction of nuclear RNA export or import, if present. In some embodiments of the method, the RNA-binding domain of the fusion protein and the protein-binding site in the RNA are derived from viral sequences.

The invention also includes a method for detecting, in real-time, the transcription of a specific gene. The method includes providing a eukaryotic cell that contains: a DNA encoding an RNA that includes a protein-binding site, and a nucleic acid encoding a fusion protein. The fusion protein includes a fluorescent domain and an RNA-binding domain that binds to the protein-binding site. The method further includes detecting a focus of fluorescence, the focus being from a multiplicity nascent RNA molecules, each nascent RNA molecule being bound to one or more fusion protein molecules. In some embodiments, the fusion protein includes a nuclear export signal domain. The nucleic acid encoding the fusion protein can be transiently expressed from a vector introduced into the cell.

Unless otherwise defined, all technical and scientific terms used herein have the same meaning as commonly understood by one of ordinary skill in the art to which this invention belongs. In case of conflict, the present application, including definitions will control. All publications, patent applications, patents, and other references mentioned herein are incorporated by reference.

Although methods and materials similar or equivalent to those described herein can be used in the practice or testing of the present invention, the preferred methods and materials are described below. The materials, methods, and examples are illustrative only and not intended to be limiting. Other features and advantages of the invention will be apparent from the detailed description, and from the claims.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIGS. 1A–1C. FIG. 1A is a schematic diagram of the NLS-MS2-GFP fusion protein. FIG. 1B is a schematic diagram of the nucleic acid construct used for expression of an NLS-MS2-GFP fusion protein and an ASH1 lacZ reporter mRNA in a yeast system. FIG. 1C is a schematic diagram of the nucleic acid construct used for expression of an NLS-MS2-GFP fusion protein and an ADHII lacZ reporter mRNA in a yeast system. A lacZ-ASH1 reporter RNA was used to demonstrate RNA movement/localization in living cells. A lacZ-ADHII reporter RNA was used as a negative control for rapid movement and localization. The reporter mRNAs contain six binding sites for the coat protein of the bacterial phage MS2. The 3'UTRs were either from the ASH1 gene, to induce mRNA localization at the yeast bud tip, or, from the ADHII gene, as a negative control. In addition, a nuclear localization signal (NLS) followed by an HA tag, was introduced at the N-terminus of the fusion protein, so that that only the fusion protein bound to its target, the reporter RNA, would appear in the cytoplasm.

DETAILED DESCRIPTION OF THE INVENTION

Figure 2:
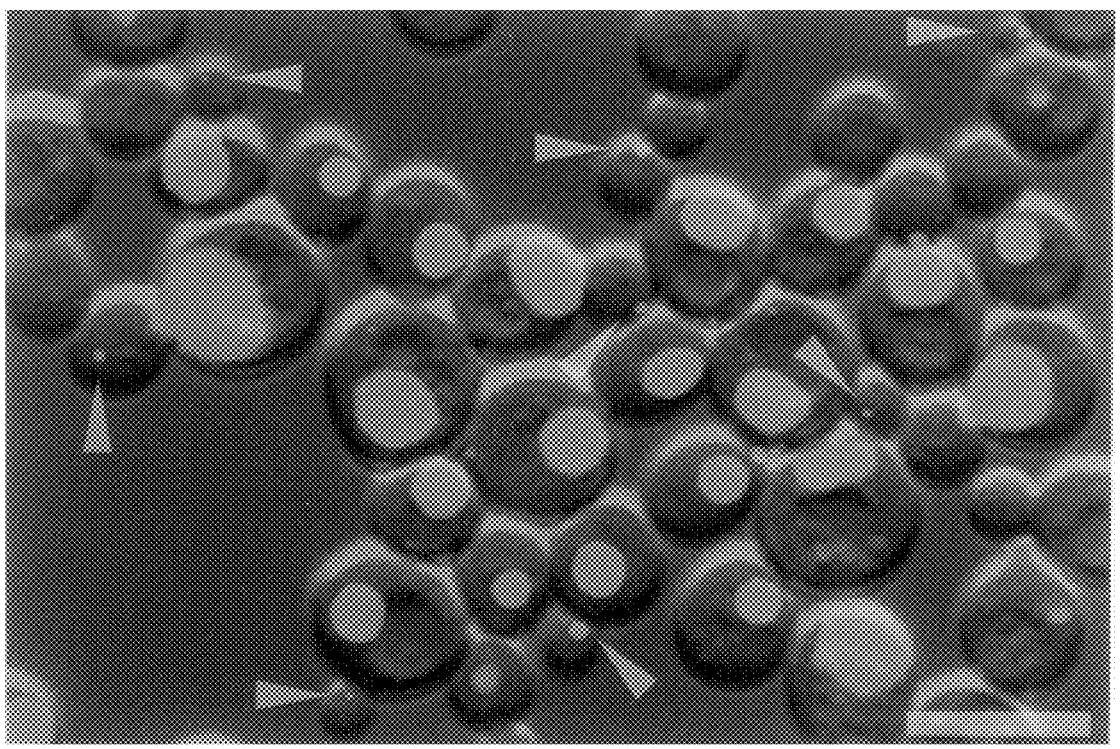
FIG. 2 is a color photomicrograph showing live cells expressing the NLS-MS2-GFP fusion protein, and the lacZ-ASH1 reporter mRNA, which contained six MS2 binding sites. Arrows indicate some of the particles, usually in the yeast bud. Bar=5 µm.

A DNA encoding the visualized RNA can be obtained readily from any suitable source using conventional recombinant DNA technology as necessary. The examples provided below involve visualizing RNA molecules engineered to include a lacZ coding region and a yeast ASH1 3' UTR containing intracellular localization signals. In the examples, the RNA molecules are visualized in yeast cells. It will be appreciated, however, that the methods of this invention are generally applicable to different RNAs and different eukaryotic cells.

The invention can be used to visualize RNAs whose movement depends on particle formation and RNAs that move without particle formation. Moreover, the invention is useful for visualizing non-localized RNAs, as well as localized RNAs. In some embodiments, the RNA to be visualized encodes a separately detectable polypeptide, e.g., β-galactosidase. Choosing or designing an RNA suitable for visualization according to this invention, and obtaining a DNA encoding the chosen RNA is within ordinary skill in the art.

For some RNAs in some cell types, RNA localization may be partially or completely dependent upon trans-acting localization factors. Therefore, in some embodiments of the invention, localization factors are present in the living cells in which the RNA is visualized. Localization factors are exemplified by the products of the she genes in yeast. These are cytoplasmic factors. Nuclear factors exporting the RNA are present in all eukaryotic cells.

The RNA to be visualized contains at least one, and preferably a multiplicity of protein-binding sites. In some embodiments of the invention, from 5 to 10 sites are suitable. In other embodiments, from 10 to 50 binding sites will be suitable. In yet other embodiments, more than 50 binding sites, i.e., up to several hundred, may be desirable. In general, increasing the number of binding sites in the RNA increases fluorescence signal strength due to an increased number of fluorescent domains bound per RNA molecule. Some RNAs already contain suitable protein-binding sites. DNAs encoding such RNAs can be used in this invention without incorporation of an exogenous protein-binding site. When the RNA to be visualized does not already contain a suitable protein-binding site, a suitable exogenous protein-binding site is incorporated into a DNA encoding the RNA.

The protein-binding site is a nucleotide sequence. Preferably, a single protein-binding site consists of a single, contiguous region of RNA, e.g., a stem-loop structure. Preferably, the length of the single, contiguous region of RNA is less than 100 nucleotides, more preferably it is less than 50 nucleotides, and most preferably, it is between 15 and 25 nucleotides. Preferably, the binding interaction between the protein-binding site and the binding domain displays high specificity, which results in a high signal-to-noise ratio.

A preferred protein-binding site is the bacteriophage MS2 binding site. Complete MS2 nucleotide sequence information can be found in Fiers et al., *Nature* 260:500–507 (1976). Additional information concerning the MS2 sequence-specific protein-RNA binding interaction appears in Valegard et al., *J. Mol. Biol.* 270:724–738 (1997); Fouts et al., *Nucleic Acids Res.* 25:4464–4473 (1997); and Sengupta et al., *Proc. Natl. Acad. Sci. USA* 93:8496–8501 (1996).

Other binding site/binding domain pairs can be used instead of the MS2-derived pair. A second useful binding site/binding domain pair is the hairpin II of the U1 small nuclear RNA and the RNA-binding domain of the U1A spliceosomal protein (Oubridge et al., *Nature* 372:432–438 (1994). A third useful alternative binding site/binding domain pair is the protein IRP1 and its RNA target, the IRE (Klausner et al., *Cell* 72:19–28 (1993); Melefors et al., *Bioessays* 15:85–90 (1993). The IRE is a stem-loop structure found in the untranslated regions of mRNAs encoding certain proteins involved in iron utilization, and it binds specifically to IRP1. A fourth useful alternative binding site/binding domain pair is HIV REV and RRF. A fifth useful alternative binding site/binding domain pair is a zipcode binding protein and a zipcode RNA element (Steward et al, supra). A sixth useful alternative binding site/binding domain pair is a box C/D motif and box C/D snoRNA family-specific binding protein (Samarsky et al., *EMBO J.* 17:3747–3757 (1998).

In addition, the protein-binding site can be an aptamer produced by in vitro selection. An aptamer that binds to a protein (or binding domain) of choice can be produced using conventional techniques, without undue experimentation. Examples of publications containing useful information on in vitro selection of aptamers include the following: Klug et al., *Mol. Biol. Reports* 20:97–107 (1994); Wallis et al., *Chem. Biol.* 2:543–552 (1995); Ellington, *Curr. Biol.* 4:427–429 (1994); Lato et al., *Chem. Biol.* 2:291–303 (1995); Conrad et al., *Mol. Div.* 1:69–78 (1995); and Uphoff et al., *Curr. Opin. Struct. Biol.* 6:281–287 (1996).

In some embodiments of the invention, the protein-binding site(s) is (are) located in the 3'UTR of the RNA to be visualized. However, the location of the protein-binding site(s) can be elsewhere in the RNA molecule. The RNA can contain other genetic elements, e.g., one or more introns, stop codons, and transcription terminators. In addition, the DNA encoding the RNA contains a promoter operably linked to the transcribed region.

The invention utilizes a fusion protein that includes at least two domains. One domain is a fluorescent domain. A preferred fluorescent domain is derived from a GFP. Naturally-occurring GFPs cause bioluminescence, e.g., in the jellyfish *Aequorea victoria*. In GFPs, fluorescence is produced by the interaction of modified amino acids in the GFP polypeptide chain. Formation of the GFP fluorophore is species independent, but GFPs can be modified through mutagenesis to optimize their function in different species. See, e.g., Cubitt et al., "Understanding, improving and using green fluorescent proteins," *Trends. Biochem. Sci.* 20:488–455 (1995). When a GFP embodiment of the invention is used in yeast, preferably the GFP domain of the fusion protein is encoded by a yeast-optimized version of a GFP cDNA. See, e.g., Cormack et al., *Microbiology* 143:303–311 (1997). Variants of GFP include blue fluorescent protein (BFP), yellow fluorescent protein (YFP), and cyan fluorescent protein (CFP).

The second domain of the fusion protein is an RNA-binding domain. This domain recognizes and interacts with the protein-binding site (in the RNA discussed above) in a specific binding interaction, under physiological conditions. A preferred RNA-binding domain is derived from the bacteriophage MS2 coat protein (capsid), which binds with high specificity to a unique site on MS2 RNA. See Fiers et al. (supra), Valegard et al. (supra), Fouts et al. (supra); and Sengupta et al., (supra). Other proteins containing RNA-binding domains are discussed above.

In some embodiments, the fusion protein includes a third domain that causes intracellular localization of the fusion protein when the fusion protein is not bound to its RNA target. Examples of intracellular localization domains include nuclear localization signal (NLS) domains, nuclear export signal (NES) domains, and nucleolar targetting domains. Various NLS sequences are known in the art, any of which can be used in the invention. A preferred NLS is derived from SV40, a well-known simian virus. A useful NES can be derived from human immunodeficiency virus (HIV) REV sequences.

When the fusion protein contains an NES domain, fluorescence is detected inside the nucleus where the protein is bound to its target RNA. In cases where the RNA is undergoing biosynthesis at the site of its gene (transcription site), the fluorescence is most intense at the transcription site. Thus, the site of active transcription of a specific gene in a living cell is visualized.

A fusion protein containing an REV-derived NES can be used as a tool to evaluate therapeutic agents that interdict HIV export. To do so, one measures flow of the REV-derived NES-containing fusion protein out of the nucleus, in the presence of a reporter RNA containing the protein-binding site known as "RRE" (REV-Responsive Element).

If the fusion protein does not include an intracellular localization domain, or if it contains an NLS, binding of the fusion protein to its RNA target can be indicated by a low fluorescence level in the nucleus (relative to the fluorescence level in the cytoplasm), when the RNA is in excess. In this situation, decreased nuclear fluorescence results from the fusion protein being dragged out of the nucleus by exiting RNA to which the protein is bound. Decreased nuclear or cytoplasmic fluorescence may be advantageous when the fusion protein is employed in cells subjected to flow sorting.

When the RNA includes a C/D box as well as a protein-binding site recognized by the fusion protein's binding domain, the RNA and fusion protein can be used in assays to screen for drugs that affect intranuclear targeting or nucleolar function.

DNAs useful to encode and express the reporter RNA (containing one or more protein-binding sites) and the fusion protein are constructed using conventional recombinant DNA techniques. Such techniques are well known in the art, and can be found in standard references such as the following: Sambrook et al., *Molecular Cloning—A Laboratory Manual* (2nd Ed.), Cold Spring Harbor Laboratory Press (1989); Innis et al. (eds.) *PCR Protocols—A Guide to Methods and Applications*, Academic Press, San Diego, Calif. (1990); Perkin-Elmer manual for PCR. Numerous DNAs containing useful coding sequences, expression control sequences, and restriction endonuclease sites to facilitate manipulation, are commercially available.

The DNA sequences required for expression of the RNA to be visualized (reporter RNA), and expression of the fusion protein, can be incorporated into a single vector. Preferably, however, the sequences are incorporated into two separate vectors. Vectors used in the invention are selected for compatibility with the cells in which they will be used. Expression vectors designed for use in particular cell types, with convenient restriction sites to facilitate the cloning of inserts, are commercially available and can be used in the invention. Preferably, the promoters used to drive expression of the RNA and the fusion protein are chosen so that the RNA expressed is in excess relative to the fusion protein.

In the practice of this invention, fluorescence microscopy image acquisition and processing can be carried out using conventional optical systems, computer hardware, and software. Image acquisition systems for use in the invention can be devised by the skilled person or obtained commercially. Suitable image capture software includes CellSCAN™ software (Scanalytics, Fairfax, Va.). Similarly, video data capture and processing can be carried out using convention hardware and software. Software useful with video data includes NIH Image (National Institutes of Health, Bethesda, Md.). It is envisioned that automated scanning procedures can be used with this invention, including microwell plate readers and flow cytometers.

Automation, however, is not required. Microscopic visual analyses will always be feasible.

The methods described here for visualizing RNA movement in living cells are generally applicable to the investigation of any RNA-protein complex, such as those involved in RNA processing, nuclear export, or intranuclear targeting.

The invention is further illustrated by the following experimental examples. The examples are provided for illustration purposes only, and they are not to be construed as limiting the scope or content of the invention in any way.

EXAMPLES

A two-plasmid system was constructed and tested successfully in yeast. In one plasmid, a GFP cDNA sequence was fused to coding sequences for the single-stranded RNA phage capsid protein MS2 (Fouts et al., supra). A nuclear-localization signal was engineered into the fusion protein (FIG. 1A). This caused the fusion protein to be restricted to the nucleus if not complexed to RNA. The fusion protein was expressed from the strong constitutive GPD promoter (Schena et al., "Guide to yeast genetics and molecular biology," in Methods in Enzymology, Gutherie et al., eds., Academic Press, New York (1991), pp. 389–398).

The second plasmid encoded a reporter RNA containing an ASH1 mRNA 3'UTR fused to a lacZ coding region (Long et al, Science 277:383–387 (1997)). Six MS2 binding sites, each consisting of a 19 nucleotide RNA stem-loop (Valegard et al, supra) were inserted downstream of the lacZ coding region (FIG. 1B). The cluster of MS2 binding sites provided for amplification of the GFP fluorescence signal due to binding of up to six fusion proteins, each containing a GFP domain. Transcription of the reporter RNA was under control of a galactose inducible promoter, as described in Long et al., RNA 1:1071–1078 (1995)).

Yeast cells expressing both the GFP-MS2 chimera and the ASH1 reporter contained a single, bright "particle" that was usually localized at the bud tip (FIG. 2).

To confirm that particle formation and localization were dependent on the ASH1 3'UTR in the reporter RNA, the ADHII 3'UTR was substituted in place of the ASH1 3'UTR. It was known that the ADHII 3'UTR sequence was unable to localize a reporter RNA to the bud tip. When the fusion protein was co-expressed with the RNA containing the ADHII 3'UTR, GFP fluorescence was diffuse, throughout the cytoplasm.

To confirm that the brightly fluorescent particles represented from the NLS-MS2-GFP fusion protein bound to the lacZ-ASH1 reporter RNA, fluorescence in situ hybridization was performed, using probes specific for lacZ. In cells expressing the lacZ-ASH1 reporter, the reporter mRNA colocalized with the fusion protein in the particle. When the lacZ-ADHII reporter RNA was used, in situ hybridization to lacZ sequences showed a diffuse reporter RNA distribution, which colocalized with the fluorescence signal from the fusion protein. When the fusion protein was expressed in cells without any reporter mRNA present, or co-expressed with an RNA lacking MS2 binding sites, GFP fluorescence was mainly restricted to the nucleus.

To determine whether the fusion protein artifactually induced particle formation, the MS2 binding sites were deleted from the lacZ-ASH1 reporter. In situ hybridization (following galactose induction) using lacZ probes revealed reporter RNA concentrated in a particles in many cells. The fusion protein was not similarly concentrated.

In contrast to the single particles observed with the lacZ-ASH1 reporter RNA, endogenous yeast ASH1 mRNA localized in a number of spots forming a crescent at the bud tip (detected by in situ hybridization).

In control cells, e.g., cells without reporter RNA, dim GFP signals were seen occasionally. These dim signals were not scored as particles because of their relative dimness, and because they never localized in the bud. The fluorescence intensity of the dim signals was approximately an order of magnitude below that of the particles formed in the presence of the ASH1 3'UTR. These dim signals may have represented aggregation of the fusion protein, even though we used a mutant version of MS2 reported to be deficient in self-assembly (Lim et al., Nucl. Acids Res. 22:3748–3752 (1994)).

Experimental results indicated that the ASH1 3'UTR facilitated the formation of a multi-molecular RNA particle. These particles were observed in the mother cell, and occasionally they were seen moving from the mother to the daughter cell. Therefore, they were deemed likely to be the vehicle by which ASH1 mRNA normally localizes in yeast. Because of the bright particles, localization was easily determined.

Yeast she mutants were known to be defective in ASH1 RNA localization (Long et al., 1997, supra; Takizawa et al., Nature 389:90–93 (1997)). Therefore, we tested she mutants for particle localization. In the she mutant strains, the number of particles was significantly decreased compared to the wild-type. The relatively few particles that formed failed to localize. In a she 5 mutant strain, the particle stayed at the bud neck. In a she3 mutant strain, the single, bright particles dispersed into many smaller particles, none of which localized. In a she1/myo4 mutant strain, particles which formed stayed in the mother. In a she2 mutant strain, particles were almost completely absent. This confirmed that particle observation was a surrogate assay for RNA localization.

Since the particles were bright enough to be followed in living cells, we observed their movement in real time, using video microscopy. This allowed us to ascertain whether the myosin directly transported the particle from mother to daughter cells. When a moving particle was identified, its movement was analyzed for up to four minutes. Movement was observed in about half of the wild type cells.

Although most of the particles were localized at or near the bud tip, they were occasionally observed moving from the mother cell to the bud. This movement sometimes occurred bidirectionally, with the particle reversing toward (but not into) the mother, and then back to the bud tip. In the mother cell, sometimes the particle moved around randomly and then accelerated through the bud neck, where velocity was the highest (net displacement per unit of time). Once in the bud, the particle moved in the distal region and occasionally stalled at the bud tip for periods exceeding one minute.

Figure 3:
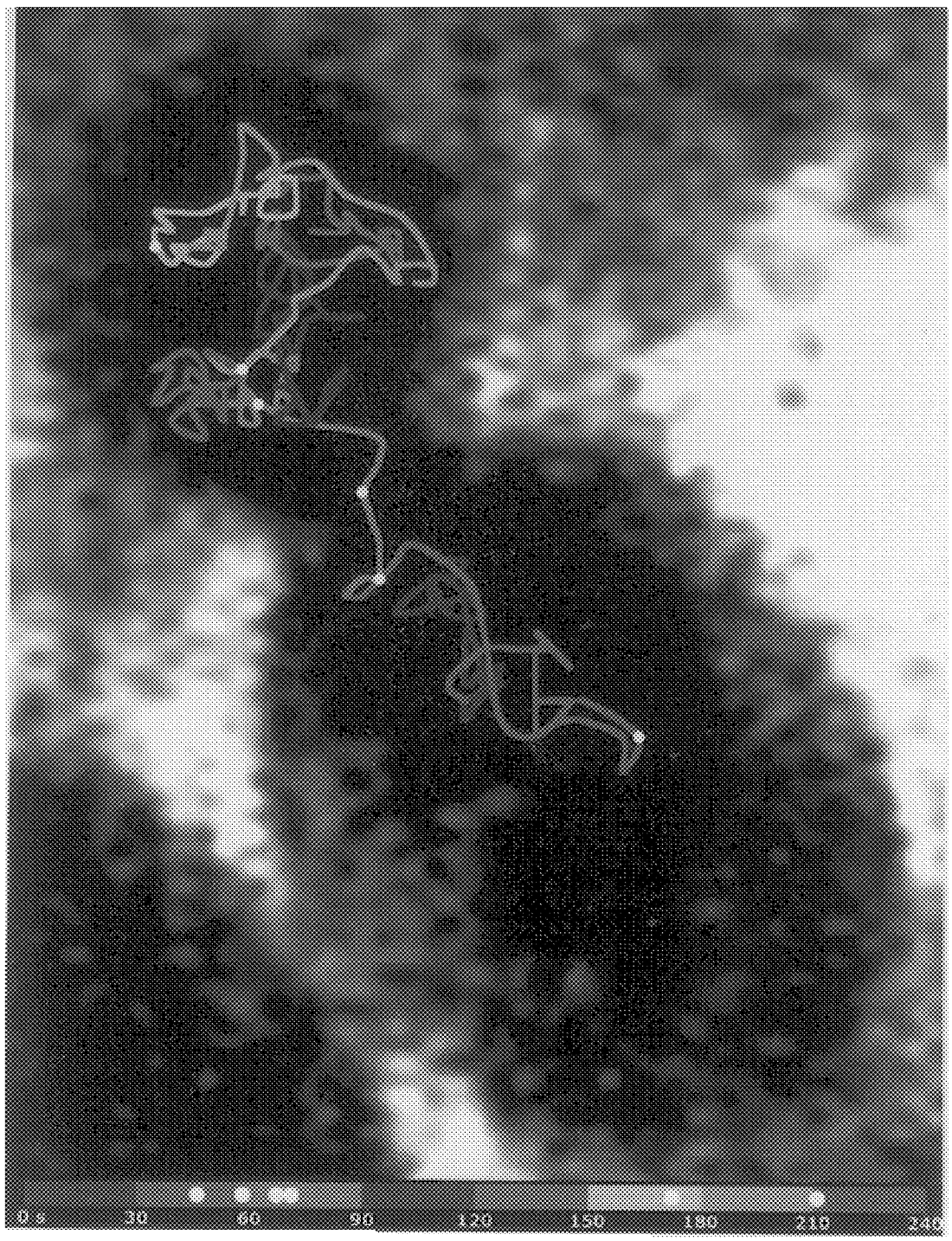
FIG. 3 is a color schematic diagram tracing the path of an RNA-containing particle in a yeast mother cell and bud (43 µm per 240 seconds). Particle movement was analyzed in a wildtype yeast strain (K699) expressing both the lacZ-ASH1 reporter RNA and the NLS-MS2-GFP fusion protein. Observation was conducted using epifluorescence and bright field microscopy. A cell with minimal nuclear signal was chosen so as not to obscure the particle. Movement of the particle was recorded with a video camera linked to a VCR. During the period of observation, the 30-second intervals are represented beginning with the coolest colors (purple) and proceeding to the hottest colors (red). The particle spent 180 out of 240 seconds in the bud, and about 60 seconds localized at or near the bud tip.

Movement of one of the wildtype particles traveling from mother cell to bud was analyzed in detail. The movement was generally directional, but the particle wandered over a path five times longer than the shortest possible distance to the bud tip. This travel path is shown in FIG. 3. The particle moved at velocities varying between 200 and 440 nm/sec (averaged over a moving window of 3 seconds). The localization time (mother to bud tip) for the particle was 128 seconds. Because of the short time required for localization, the movement of the RNA was a rare event in the steady-state population. This short time for RNA transport emphasized the importance of using living cells to investigate the process of localization.

The visualization of RNA movement in a living cell presented a dynamic view of the localization mechanism. Several insights into the localization process resulted from this approach. A first insight was that RNA transport occurred via a macromolecular complex, a particle. A second insight was that the speed of movement of the RNA-containing particle was such that it moved to its destination within a few minutes. A third insight was that genes required for localization appear to interact with the RNA via the particle.

The transport of the reporter could be visualized because of the formation of a particle. Because the particle formation was dependent on specific sequences in the ASH1 3'UTR sufficient for directing a LacZ reporter RNA to the bud, and because it could not localize in she mutant strains, the particle served as a reporter for localization. She proteins and sequences from the ASH1 mRNA 3'UTR participated in particle formation. The particle may have been directly associated with myosin, possibly through She3p.

Yeast Genotypes

The following yeast genotypes were used in the experiments described here.

wild type: k699 genotype: (Matα, his3-11, leu2-3, ade2-1, trp1-1, ura3, ho, can1-100)

she1: K5209 genotype (Matα, his3, leu2, ade2, trp1, ura3, can1-100, she1::URA3)

she2: K5547 genotype (Matα, his3, leu2, ade2, trp1, ura3, HO-ADE2, HO-CAN1, she2::URA3)

she3: K5235 genotype (Matα, _his3, leu2, ade2, trp1, ura3, can1-100, she3::URA3)

she4: K5560 genotype (Matα, his3, leu2, ade2, trp1, ura3, she4::URA3)

she5: K5205 genotype (Matα, his3, leu2, ade2, trp1, ura3, can1-100, she5::URA3)

Reporters containing MS2 binding sites

Two repeats of a high affinity MS2 binding site was amplified by PCR from the pIIIA-MS2-2 plasmid (Sengupta et al., supra) with the following oligonucleotides:

5' CTAGCTGGATCCTAAGGTACCTAATTGC-CTAGAAAACATGAGGA (SEQ ID NO: 1), and

5' ATGCTAAGATCTAATGAACCCGG-GAATACTGCAGACATGGGAGAT (SEQ ID NO:2).

The PCR product was digested with BamHI and BglII, and self-ligated in presence of the same enzyme, to multimerize the MS2 sites in head-to-tail orientation. The DNA corresponding to a six-repeat of the MS2 site was gel purified, and ligated into the BamHI and BglII sites of pSL1180 (Pharmacia), to give the plasmid pSL-MS2-6. The plasmids pXR55 (ASH1 3'UTR) and pXR2(ADHII 3'UTR) were generated (respectively) by subcloning the lacZ-ASH1 3' UTR and the lacZ-ADHII reporter constructs into the yeast vector YEplac195 (Gietz et al., Gene 74:527–534 (1988)) as a PstI/EcoRI restriction fragment generated by PCR and DNA restriction digests. The lacZ-ASH1 3' UTR cassette originated from plasmid pXMRS25. The lacZ-ADHII cassette originated from plasmid pHZ18-polyA (Long et al., RNA 1:1071–1078 (1995); Long et al., 1997 (supra). Both pXR55 and pXR2 contained the URA3 selectable marker and the 2 micron origin of replication, and expressed the reporter mRNAs from a galactose inducible promoter. Plasmid pSL-MS2-6 was digested by MscI and EcoRV, and cloned at the KpnI site of pXR55, to give pGal-lacZ-MS2-ASH1/URA. Alternatively, it was digested with BamHI and NheI and cloned between the BglII and XbaI sites and pGal-lacZ-ADHII/URA, to yield plasmid pGal-lacZ-MS2-ADHII/URA. The GAL-lacZ-MS2-ASH1 reporter cassette was then moved into YEplac 112, TRP1 selectable, 2 micron plasmid by cloning the ScaI-EcoRI fragment of pGAL-lacZ-MS2-ASH1/URA into the ScaI and EcoRI sites of pYEplac112, to give pGAL-lacZ-MS2-ASH1/TRP.

Fusion protein vector construction

A yeast-optimized version of the GFP cDNA (Cormack et al., supra) was amplified by PCR with the following oligonucleotide primers:

5' GTATCAGCGGCCGCTTCTAAAGGTGAAGAATTA (SEQ ID NO: 3)(yGFP/5'), and

5' TGACCTGTCGACTTTGTACAATTCATCCAT (SEQ ID NO: 4)(yGFP/3').

The resulting PCR product was then digested with NotI.

A plasmid containing the HA-tagged MS2 mutant protein dlFG was obtained from Philippe Couttet (IJM, Paris). This cDNA was PCR amplified with the following oligonucleotides:

5' TCAGTCGCGGCCGCGTAGATGCCGGAGTTT (MS2/3')(SEQ ID NO: 5), and

5' TAGCATGGATCCACC ATGCCAAAAAAGAAAAGAAAAAGTTGGCTA CCCCTACGACGTG CCCGA (NLS-MS2/5') (SEQ ID NO: 6).

The translation start codon (ATG) followed by the SV40 nuclear localization sequence is indicated by underlining. The resulting PCR product was then digested with NotI. The two PCR products were then ligated, and the GFP-MS2 chimeric cDNA was reamplified with the GFP/3' and the NLS-MS2/5' oligonucleotides. The resulting PCR product was then digested with BamHI and SalI, and ligated into the corresponding site of the LEU2 selectable, 2 micron pG14 plasmid (Lesser et al., Genetics 133:851–863 (1993); gift of J. Warner) to give pGFP-MS2/LEU.

Fusion protein expression

The strain K699 (Matα, trp1-1, leu2-3, his3-11, ura3, ade2-1, ho, can1-100) was transformed with various combinations of the episomal vectors described above and selected on the appropriate selection media to maintain the plasmids. Yeast cells were then grown to mid-log phase in synthetic media containing 2% raffinose. Cells were subsequently induced with 3% galactose for 3 hours or the indicated times, to induce expression of the reporter mRNA. Due to the variable expression levels of the two plasmids, some cells had particles without much GFP nuclear signal, while other cells had strong GFP signal without visible particles.

Measurement of particle brightness

Particles displayed a range of intensities. The single, bright particles in cells with the ASH1 reporter, and the much weaker particulate signals in the control cells, were digitally imaged, using Cellscan software (Scanalytics, Va.). Total fluorescence intensity was measured. The single, bright particle had a fluorescent intensity 10.7 times brighter than the relatively dim particulate signals observed in controls. Thus, particle signals and non-particle signals were easily distinguished.

Particle counts were scored by three individuals. In different isolates of the wildtype strain, fixed cells containing the bright, single particles ranged from 54% to 68%. Localization in these cells ranged from 64% to 78%.

In situ hybridization

Yeast cells were processed for in situ hybridization essentially as described in Long et al., 1995 (supra); and Long et al., 1997 (supra), except that the hybridization mixture and the wash solutions contained only 10% formamide. The oligo-Cy3-conjugated probes were also as described in Long et al., 1995 and Long et al., 1997.

Cells were prepared for immunofluorescence as for in situ hybridization. After permeabilization overnight in 70% ethanol, the cells were rehydrated in antibody buffer (2×SSC, 8% formamide) for 10 minutes at room temperature, and then incubated in antibody buffer containing 0.2% RNAse DNAse free BSA and an anti-myc antibody (gift from K. Nasmyth) diluted 1:5, for 1 hour at 37° C. Cells were then washed for 30 minutes at room temperature in antibody buffer, and further incubated for 1 hour at 37° C. with a Cy3 conjugated anti-mouse secondary antibody diluted 1:700, in antibody buffer. Cells were mounted in mounting media as described in Long et al., 1996 (supra) and Long et al., 1997 (supra), after a final 30-minute wash at room temperature, in antibody buffer.

Image acquisition and processing

Images were captured using CellSCAN software (Scanalytics, Fairfax, Va.) on an Optiplex GXpro computer (Dell, Austin, Tex.) with a CH-250 16-bit, cooled CCD camera (Photometrics, Tuscon, Ariz.) mounted on a Provis AX70 fluorescence microscope (Olympus, Melville, N.Y.) with a PlanApo 60x, 1.4 NA objective (Olympus) and HiQ bandpass filters (Chroma Technology, Brattleboro, Vt.). The fluorescence illumination was controlled by the software using a Uniblitz VS25 shutter (Vincent Associates, Rochester, N.Y.). When images were restored, a three-dimensional data set, composed of 20–25 images separated by 200 nm in the axial direction, was acquired and deconvolved with an acquired point spread function (PSF) using EPR software (Scanalytics). The software controlled the axial position of the objective using a PZ54 E piezoelectric translator (Physik Instrumente, Costa Mesa, Calif.). The PSF is a data set, composed of 40–50 images separated by 200 nm in the axial direction, of a fluorescent microsphere (Molecular Probes, Eugene, Oreg.) that was 200 nm in diameter. A single median plane was recorded for blue filtered images.

Colocalization of GFP particle and She1/MYo4myc

Twenty cells were analyzed for colocalization of the particle and She1myc. Thirty optical sections of each cell were taken, and the red and green images were superimposed for each image plane. The number of particles colocalizing with She1myc in the same plane were counted. About half (45%) were colocalized with She1myc. For a control, wild type cells containing GFP particles without She1myc were evaluated by identical methods. No colocalization was observed with the immunofluorescent antibodies.

Cloning and Epitope Tagging of SHE Genes

The SHE genes were isolated from yeast genomic DNA (strain K699) by PCR. Primers were designed to obtain a PCR fragment of the respective SHE gene to include 1 kb of the promoter as well as 1 Kb of the 3'-UTR region. The cloned SHE genes were subcloned into YEplac112 and YCplac22 and transformed into yeast strains disrupted for the respective gene and tested for functionality by rescue of ASH1 mRNA localization as determined using fluorescence in situ hybridization.

A unique restriction site was introduced after the corresponding start codon or in front of the respective stop codon for each of the SHE genes (except SHE1) using a splicing through overlap extension strategy. Four primers were designed for each SHE gene. This gave rise to two PCR fragments that had an overlapping sequence containing a single restriction site at the N-terminal or C-terminal part of the gene. These fragments served as template in a second PCR step used to amplify the final fragment, which was cloned in YEplac112.

Three Myc epitopes were introduced in these unique sites using BamHI (in the case of SHE3) or XbaI (SHE2) fragments of a Myc epitope cassette (from plasmid pC3003, gift from K. Nasmyth). In the case of SHE1/MYO4, a C-terminal SpeI site (25 amino acids upstream from the stop codon) was used to subclone a SpeI fragment of a c-Myc epitope cassette (from plasmid pC3390, gift from K. Nasmyth) containing nine Myc epitopes. Expression of the Myc-epitope tagged proteins was also shown by Western blots.

After demonstrating functionality, SHE-myc plasmids were transformed into K699, containing a wildtype locus for each SHE gene with the GFP-reporter plasmids for colocalization studies.

Video analysis

Live cells were mounted between two coverslips and visualized on an inverted microscope (Nikon, Melville, N.Y.) with a PlanApo 60x, 1.4 NA, Ph4 objective (Nikon) using simultaneous brightfield and epifluorescence illumination. Live video was captured using a C2400 Silicon Intensified Tube Camera (Hamamatsu, Oakbrook, Ill.) with a 2x eyepiece and recorded on video tape in S-VHS format. Appropriate sequences from the tape were digitized at a rate of one frame per second using NIH Image software (NIH, Bethesda, Md.) with a frame size of 640×480 pixels on a Power Macintosh 7600 computer (Apple, Cupertino, Calif.) with S-Video interface. Using NIH Image, the particle's position in each captured frame was tabulated and then used to calculate distance travelled and speed.

Motor analysis

Four minutes of video analysis of a specific particle moving from mother cell to bud was analyzed at one-second intervals. The movement was then averaged over a moving time window of three-second time points, and spatially filtered to require a total net travel of five pixels (about 0.5 $\mu$m) during this time window. The wild-type movement throughout the time frame resulted in 15 of these 3-second 'jumps' at intervals ranging from 5 to 30 seconds.

Distances moved during the time frame ranged from 0.6 to 1.4 $\mu$m. Average speeds per 'jump' ranged from 200 to 440 nm/sec. The she1 deletion strain showed no movement when subjected to this spatial filtering. Effectively, this approach subtracted the background she1 movement from the wildtype to reveal the motility characteristics of the She1/Myo4p.

Visualization of RNA not incorporated into particles

The bright particle observed in yeast may not be present in cells other than yeast cell, e.g., in vertibrate cells. RNA not incorporated into particles is visualized as follows. Forty-eight MS2 binding sites are incorporated into an actin mRNA. When all the MS2 binding sites are loaded with, i.e., bound to, a fusion protein containing a GFP domain and an MS2 binding domain, a single mRNA molecule is visually detectable by GFP fluorescence, using techniques such as those described in Femino et al., *Science* 280:585–590 (1998).

Other embodiments are within the following claims.

We claim:

1. A method for visualizing an RNA in a living cell, comprising:

providing a DNA encoding the RNA, which RNA comprises a naturally-occurring protein-binding sequence or an engineered protein-binding sequence;

providing a nucleic acid encoding a fusion protein, which fusion protein comprises a fluorescent domain and an RNA-binding domain that binds to the protein-binding sequence;

introducing the DNA encoding the RNA, and the nucleic acid encoding the fusion protein, into a eukaryotic cell so that the DNA and the nucleic acid are expressed in the cell; and detecting fluorescence in the cell, the fluorescence being from the fusion protein bound to the RNA;

thereby visualizing the RNA in the living cell.

2. The method of claim 1, wherein the fusion protein further comprises a domain that causes intracellular localization of the fusion protein when the fusion protein is not bound to its RNA target.

3. The method of claim 1, wherein the RNA comprises a multiplicity of protein-binding sequences.

4. The method of claim 1, wherein the protein-binding sequence is located in the 3' untranslated region of the RNA.

5. The method of claim 1, wherein the RNA-binding domain is derived from an MS2 protein, and the protein-binding sequence is a bacteriophage MS2 binding site.

6. The method of claim 1, wherein the fluorescent domain is derived from green fluorescent protein.

7. The method of claim 1, wherein the DNA encoding the RNA, and the nucleic acid encoding the fusion protein, are provided on separate DNA vectors.

8. The method of claim 1, wherein the cell comprises a trans-acting localization factor that affects localization of the RNA.

9. The method of claim 1, wherein the cell is a yeast cell.

10. The method of claim 2, wherein the intracellular localization domain is selected from the group consisting of a nuclear localization signal domain and a nuclear export signal domain.

11. The method of claim 10, wherein the intracellular localization domain is a nuclear localization signal domain, and the fluorescence from the fusion protein bound to the RNA is detected outside the nucleus.

12. A method for screening a DNA library to detect a DNA encoding an RNA comprising a protein-binding sequence, the method comprising:

providing a eukaryotic cell that expresses a fusion protein comprising a fluorescent domain and an RNA-binding domain that binds to a protein binding sequence;

transforming the test cell with a candidate DNA from the DNA library; and detecting the fusion protein bound to an RNA comprising the protein-binding sequence, if present, by measuring fluorescence, thereby detecting an RNA comprising the protein-binding sequence.

13. The method of claim 12 wherein the test cell does not express an endogenous protein that binds to the protein-binding sequence.

14. The method of claim 12, wherein the DNA encoding the RNA comprises a multiplicity of protein-binding sequences.

15. The method of claim 12, wherein the RNA-binding domain is derived from a bacteriophage MS2 protein, and the protein-binding sequence is a bacteriophage MS2 binding site.

16. The method of claim 12, wherein the fluorescent domain is derived from green fluorescent protein.

17. The method of claim 12, wherein the fusion protein further comprises an intracellular localization domain.

18. A screening method for identifying a compound that inhibits nuclear RNA export or import, the method comprising:

providing a eukaryotic test cell that:
(a) expresses a DNA encoding an RNA, which RNA comprises a protein-binding sequence; and (b) expresses a fusion protein comprising a fluorescent domain and an RNA-binding domain that binds to the protein-binding sequence in the RNA;

contacting the test cell with a candidate compound;

detecting a candidate compound-related reduction of nuclear RNA export or import, if present;

thereby identifying a compound that inhibits nuclear RNA export or import.

19. The method of claim 18, wherein the RNA-binding domain of the fusion protein and the protein-binding sequence of the RNA are derived from viral sequences that encode a viral RNA binding protein and an RNA sequence that is recognized and bound by that viral RNA binding protein.

20. A method for detecting, in real-time, the transcription of a specific gene, comprising:

providing a eukaryotic cell that comprises:
(a) a DNA encoding an RNA that comprises a protein-binding sequence, and (b) a nucleic acid encoding a fusion protein, which fusion protein comprises a fluorescent domain and an RNA-binding domain that binds to the protein-binding sequence;

detecting a focus of fluorescence, the focus being from a multiplicity of nascent RNA molecules, each nascent RNA molecule being bound to one or more fusion protein molecules;

thereby detecting, in real time, the transcription of a specific gene.

21. The method of claim 20, wherein fusion protein includes a nuclear export signal domain.

22. The method of claim 20, wherein the nucleic acid encoding the fusion protein is transiently expressed from a vector introduced into the cell.

* * * * *

SEQUENCE LISTING

<160> NUMBER OF SEQ ID NOS: 6

<210> SEQ ID NO 1
<211> LENGTH: 44
<212> TYPE: DNA
<213> ORGANISM: Bacteriophage MS2

```
<400> SEQUENCE: 1
ctagctggat cctaaggtac ctaattgcct agaaaacatg agga                44

<210> SEQ ID NO 2
<211> LENGTH: 45
<212> TYPE: DNA
<213> ORGANISM: Bacteriophage MS2

<400> SEQUENCE: 2
atgctaagat ctaatgaacc cgggaatact gcagacatgg gagat               45

<210> SEQ ID NO 3
<211> LENGTH: 33
<212> TYPE: DNA
<213> ORGANISM: Unknown
<220> FEATURE:
<223> OTHER INFORMATION: most probably a yeast

<400> SEQUENCE: 3
gtatcagcgg ccgcttctaa aggtgaagaa tta                            33

<210> SEQ ID NO 4
<211> LENGTH: 30
<212> TYPE: DNA
<213> ORGANISM: Unknown
<220> FEATURE:
<223> OTHER INFORMATION: most probably a yeast

<400> SEQUENCE: 4
tgacctgtcg actttgtaca attcatccat                                30

<210> SEQ ID NO 5
<211> LENGTH: 30
<212> TYPE: DNA
<213> ORGANISM: Unknown
<220> FEATURE:
<223> OTHER INFORMATION: most probably a yeast

<400> SEQUENCE: 5
tcagtcgcgg ccgcgtagat gccggagttt                                30

<210> SEQ ID NO 6
<211> LENGTH: 63
<212> TYPE: DNA
<213> ORGANISM: Unknown
<220> FEATURE:
<223> OTHER INFORMATION: most probably a yeast

<400> SEQUENCE: 6
tagcatggat ccaccatgcc aaaaagaaa agaaaaagtt ggctacccct acgacgtgcc    60
cga                                                             63
```